United States Patent
Saito et al.

(10) Patent No.: US 7,967,437 B2
(45) Date of Patent: Jun. 28, 2011

(54) RETINAL SCANNING IMAGE DISPLAY APPARATUS AND IMAGE DISPLAY SYSTEM

(75) Inventors: Yoshihiro Saito, Hachioji (JP); Akira Yamamoto, Yokohama (JP); Takashi Tsuyuki, Kawasaki (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 11/951,583

(22) Filed: Dec. 6, 2007

(65) Prior Publication Data

US 2008/0151185 A1  Jun. 26, 2008

(30) Foreign Application Priority Data

Dec. 8, 2006  (JP) .................................. 2006-332261

(51) Int. Cl.
  *A61B 3/10*   (2006.01)
  *A61B 3/14*   (2006.01)
(52) U.S. Cl. ......................... 351/205; 351/209; 351/221
(58) Field of Classification Search .......... 351/205–206, 351/210, 221
See application file for complete search history.

(56) References Cited

U.S. PATENT DOCUMENTS

| 5,430,509 | A | * | 7/1995 | Kobayashi | 351/221 |
| 5,703,637 | A | * | 12/1997 | Miyazaki et al. | 348/53 |
| 5,815,242 | A | * | 9/1998 | Anderson et al. | 351/221 |
| 6,302,879 | B1 | * | 10/2001 | Frey et al. | 606/12 |
| 6,967,781 | B2 | | 11/2005 | Watanabe et al. | |
| 2002/0036750 | A1 | * | 3/2002 | Eberl et al. | 351/207 |

FOREIGN PATENT DOCUMENTS

| JP | 07-135623 | 5/1995 |
| JP | 10-319342 | 12/1998 |
| JP | 2004-191962 | 7/2004 |

* cited by examiner

*Primary Examiner* — Dawayne A Pinkney
(74) *Attorney, Agent, or Firm* — Rossi, Kimms & McDowell LLP

(57) ABSTRACT

A retinal scanning image display apparatus includes a light source, a scanning unit that scans a light flux from the light source, a reflective surface that reflects the light flux from the scanning unit, and an ocular unit that guides the light flux from the reflective surface to an eye of an observer. Optical paths of the light flux scanned by the scanning unit intersect at an exit pupil position of the ocular unit, and the image display apparatus causes the scanning unit and the reflective surface to shift so that the optical paths of the scanned light flux toward the same image position are respectively moved in parallel to move the intersecting position of those optical paths. This realizes a small retinal scanning image display apparatus capable of keeping the image position substantially constant even when an observer moves their pupil.

12 Claims, 8 Drawing Sheets

PRIOR ART

PRIOR ART

RETINAL SCANNING IMAGE DISPLAY APPARATUS AND IMAGE DISPLAY SYSTEM

BACKGROUND OF THE INVENTION

The present invention relates to a retinal scanning image display apparatus that draws an image on a retina of an observer by guiding a light flux modulated in accordance with a video (image) signal to a pupil of the observer and scanning the light flux two-dimensionally.

In an image display apparatus as stated above, an image is drawn directly on the retina through the pupil of the observer by scanning laser light two-dimensionally. Among this sort of apparatuses, there is an apparatus adapted to detect the motion of the pupil of the observer and causes laser light to enter the pupil so as to follow the motion, thus avoiding the image from disappearing even when the observer moves their pupils (see Japanese Patent Laid-Open No. 7 (1995)-135623).

As shown in FIG. 6A, however, when the pupil Ea of the observer shifts (rotates) from position P10 to position P11, the converging point P10 of the image light flux La1, Lb1, and Lc1 needs to be shifted to P11 so as to keep it within the pupil Ea.

In FIG. 6A and FIGS. 6B, 6C and 7 described later, La1, La2, and La3 represent center light fluxes of an image, and Lb1, Lb2, and Lb3 and Lc1, Lc2, and Lc3 represent light fluxes at the edges of the image.

As shown in FIG. 6B, when the image light fluxes La1, Lb1, and Lc1 are shifted to be La2, Lb2, and Lc2, the incident angles of the image light fluxes to the pupil Ea will be different from than those in FIG. 6A. Therefore, the image appears displaced to the observer. To prevent this, the image light fluxes La1, Lb1, and Lc1 need to be shifted in parallel to be La3, Lb3, and Lc3, as shown in FIG. 6C.

As shown in FIG. 7, Japanese Patent Laid-Open No. 10 (1998)-319342 discloses an image display apparatus that converges light fluxes from a display panel 121 by means of a microlens array 122 and an ocular lens 123 to guide them to the pupil Ea of the observer.

This image display apparatus changes the converging position of the image light fluxes so as to follow the movement of the pupil Ea and controls the incident angles thereof to the pupil Ea to be kept constant even when the converging position is changed. In other words, the displacement of the image becomes less recognizable even when the pupil Ea moves.

More specifically, when the pupil of the observer shifts from P12 to P13, then the microlens array 122 is driven in the direction of the arrow F, so as to shift the converging position of the image light fluxes La1, Lb1, and Lc1 (La2, Lb2, and Lc2) to position P13. At the same time, the display position of the display panel 121 is shifted, so that the image light fluxes La2, Lb2, Lc2 for the pupil Ea located at P13 indicated by solid lines are in parallel with the image light fluxes La1, Lb1, and Lc1 for the pupil Ea located at P12.

Japanese Patent Laid-Open No. 2004-191962 discloses a retinal scanning image display apparatus that detects the eye direction of the observer and changes the incident angles of the image light fluxes to the pupil in accordance with the detection result.

In the apparatus disclosed in Japanese Patent Laid-Open No. 10 (1998)-319342, however, there is a need to secure an extra display area of the display panel beforehand in order to keep the incident angles of the image light fluxes to the pupil Ea constant. Therefore, there is a problem of increasing the display panel in size.

In the apparatus disclosed in Japanese Patent Laid-Open No. 2004-191962, a change of the eye direction causes a change of the image position.

BRIEF SUMMARY OF THE INVENTION

The present invention provides a small retinal scanning image display apparatus capable of keeping the image position substantially constant even when an observer moves their pupil.

As one aspect, the present invention provides a retinal scanning image display apparatus including a light source, a scanning unit that scans a light flux from the light source, a reflective surface that reflects the light flux from the scanning unit, and an ocular unit that guides the light flux from the reflective surface to an eye of an observer. Optical paths of the light flux scanned by the scanning unit intersect at an exit pupil position of the ocular unit, and the image display apparatus causes the scanning unit and the reflective surface to shift so that the optical paths of the scanned light flux toward the same image position are respectively moved in parallel to move the intersecting position of those optical paths.

As another aspect, the present invention provides a retinal scanning image display apparatus including a light source, a scanning unit that scans a light flux from the light source, first and second reflective surfaces that reflect sequentially the light flux from the scanning unit, and an ocular unit that guides the light flux from the second reflective surface to an eye of an observer. Optical paths of the light flux scanned by the scanning unit intersect at an exit pupil position of the ocular unit, and the image display apparatus causes the first and second reflective surfaces to shift so that the optical paths of the scanned light flux toward the same image position are respectively moved in parallel to move the intersecting position of those optical paths.

As still another aspect, the present invention provides a retinal scanning image display apparatus including a light source, a scanning unit that scans a light flux from the light source, a reflective surface that reflects the light flux from the scanning unit, and an ocular unit that guides the light flux from the reflective surface to an eye of an observer. Optical paths of the light flux scanned by the scanning unit intersect at an exit pupil position of the ocular unit, and the image display apparatus changes a light-emitting timing of the light source for operation of the scanning unit and causes the reflective surface to shift so that the optical paths of the scanned light flux toward the same image position are respectively moved in parallel to move the intersecting position of those optical paths.

Other aspects of the present invention will become apparent from the following description and the attached drawings.

DETAILED DESCRIPTION OF THE PREFERRED EMBODIMENTS

Exemplary embodiments of the present invention will hereinafter be described with reference to the accompanying drawings.

Embodiment 1

Figure 1:
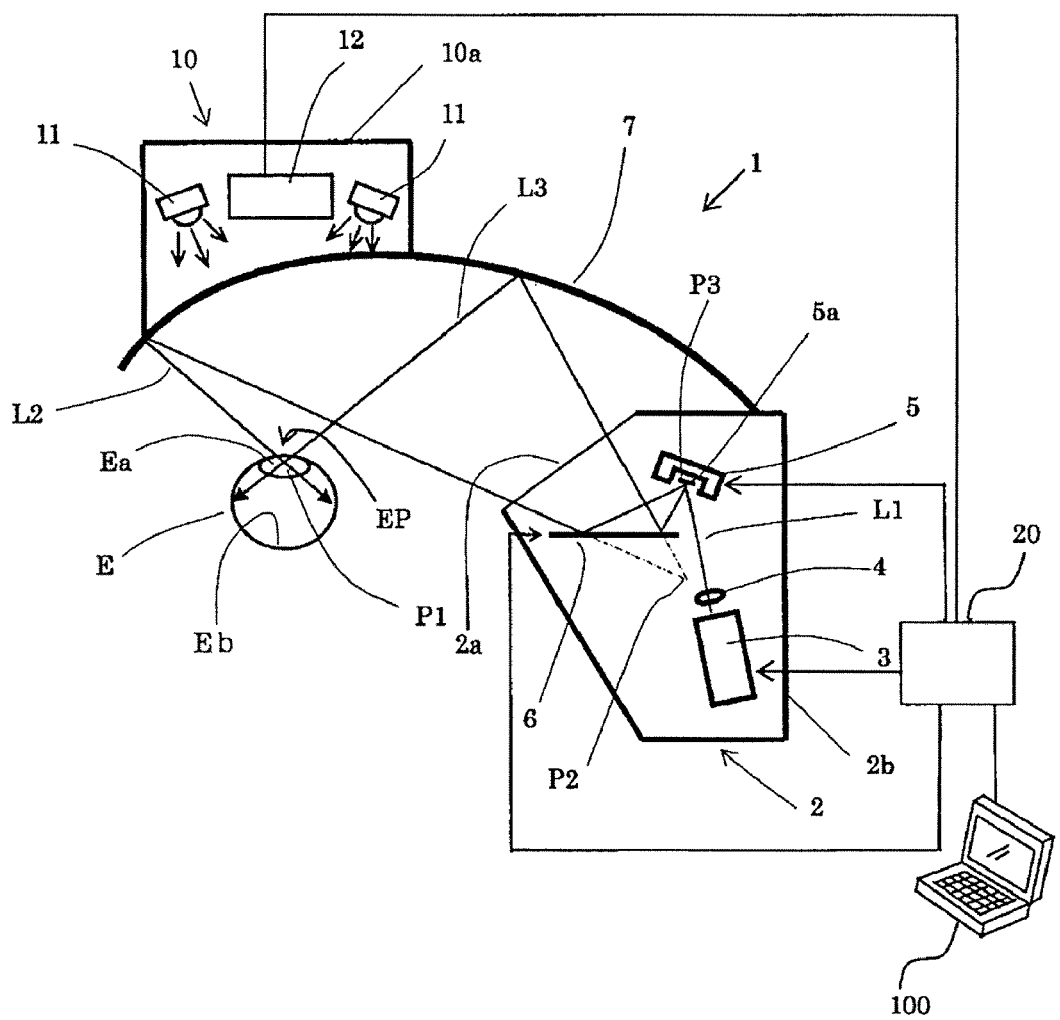
FIG. 1 shows the configuration of a retinal scanning image display apparatus that is Embodiment 1 of the present invention.

FIG. 1 shows the configuration of a retinal scanning image display apparatus that is Embodiment 1 of the present invention.

In FIG. 1, reference numeral 1 denotes an image display apparatus. The image display apparatus 1 includes a scanning part 2 that performs two-dimensional scanning of a light flux modulated in accordance with a video (image) signal from an image supply apparatus 100. The image display apparatus 1 further includes an ocular mirror 7 serving as an ocular unit that causes the optical paths of the light flux scanned by the scanning part 2 to intersect at the position of the exit pupil EP, i.e., that converges the light fluxes there.

At the position of the exit pupil EP of the ocular mirror 7 or at the vicinity thereof, a pupil Ea of an eye E of an observer is placed. The image display apparatus 1 further includes a pupil detection unit 10 and a controlling part 20, in which the pupil detection unit 10 serves as a detector that detects the motion of the eye E (pupil Ea) of the observer and the controlling part 20 controls the scanning part 2.

The controlling part 20 is connected with the image supply apparatus 100 such as a personal computer, a DVD player, or a TV tuner, and the image display apparatus 1 and the image supply apparatus 100 constitute an image display system. The controlling part 20 controls, based on the video signal (image information) input from the image supply apparatus 100, a beam modulating operation of a beam light source described later and scanning operation by a scanning unit. This is also applied to other embodiments described later.

In the scanning part 2, reference numeral 3 denotes the beam light source that emits a light flux L1 modulated in accordance with the video signal, and 4 denotes a lens that converts the light flux emitted from the beam light source 3 into a collimated light flux. Reference numeral 5 denotes the scanning unit that scans the collimated light flux two-dimensionally. The scanning unit 5 is constituted by a MEMS (Micro Electro-Mechanical System) mirror device that causes a minute scanning mirror 5a to swing reciprocally in two-dimensional directions. Alternatively, the light flux may be scanned two-dimensionally by using two scanning units each having a scanning mirror that swings reciprocally in one-dimensional direction, in which the reciprocating directions of these scanning mirrors are set crossing each other at right angles. Reference numeral 6 denotes a movable planar mirror serving as a reflective surface.

The ocular mirror 7 is a curved mirror constituted by a part of a curved member such as a spheroid with a long axis being a straight line (not illustrated) passing through two focal points P1 and P2.

The first focal point P1 of the ocular mirror 7 coincides with the exit pupil EP of the ocular mirror 7. The second focal point P2 is located at position P3 that is conjugate with the movable planar mirror 6. P3 is set at the position of the scanning mirror 5a of the scanning unit 5.

The light flux L1 emitted from the beam light source 3 is converted into a collimated light flux by the lens 4, and enters the scanning unit 5. The light flux is reflected by the scanning mirror 5a, while being scanned two-dimensionally. Then, the scanned light flux is reflected by the movable planar mirror 6, passes through a transparent window 2a of the scanning part 2 and is reflected by the ocular mirror 7, and then proceeds toward the exit pupil EP. Although the optical path of the light flux changes over time in accordance with a change of the angle of the scanning mirror 5a of the scanning unit 5, the respective optical paths pass through the exit pupil EP. In other words, the ocular mirror 7 causes the optical paths of the scanned light flux to intersect at the exit pupil EP.

As described above, the pupil Ea of the observer is placed at the exit pupil EP. Thus, the scanned light flux allows an image directly to be drawn on a retina Eb of the observer. L2 and L3 represent light fluxes forming the image, which enter the pupil Ea. Since the entering light flux has a thickness of about 1 mm in diameter, the observer can recognize the image irrespective of their eyesight.

The scanning part 2 has a hermetically sealed structure with the transparent window 2a and a cover 2b, which protects the optical system from the beam light source 3 to the movable planar mirror 6 against dust and dirt.

The pupil detection unit 10 is constituted by two LEDs 11 and a camera 12, in which the LEDs 11 emit invisible light such as infrared rays and the camera 12 takes an image of the eye E of the observer irradiated with the light from the LEDs 11. The image of the eye E captured by the camera 12 is sent to the controlling part 20. The controlling part 20 detects the pupil position by image processing.

The pupil detection unit 10 is provided on the back of the ocular mirror 7 (the opposite side to the reflective surface). The ocular mirror 7 has the property of reflecting visible light from the beam light source 3 but transmitting invisible light such as infrared rays from the LEDs 11. Therefore, the invisible light from the LEDs 11 is transmitted through the ocular mirror 7 and is applied to the eye E of the observer, and then the camera 12 takes an image of the invisible light reflected by the eye E and transmitted through the ocular mirror 7.

The pupil detection unit 10 has a hermetically sealed structure with a cover 10a and the ocular mirror 7, which protects the LEDs 11 and the camera 12 against dust and dirt.

Figure 2:
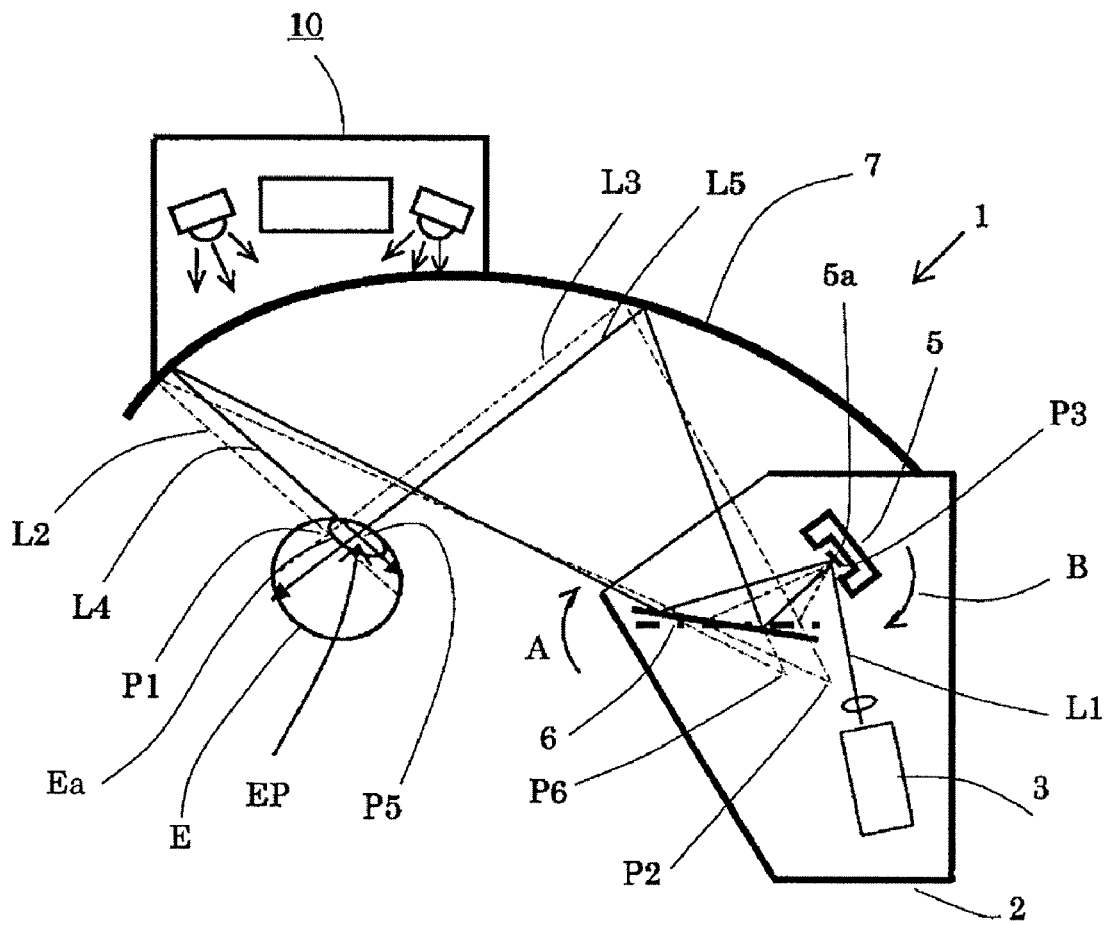
FIG. 2 shows the relationship between the movement of the pupil and the shift of the light flux in the retinal scanning image display apparatus of Embodiment 1.

FIG. 2 shows the state where the eye E of the observer rotates to right (the eye direction is shifted from the front to the right). The entering light fluxes L2 and L3 to the pupil Ea have a thickness of about 1 mm in diameter as described above. On the other hand, the diameter of the pupil is about 4 mm. Thus, when the pupil position changes as shown in FIG. 2, if the optical paths of the entering light fluxes L2 and L3 still intersect at P1 as shown in FIG. 1, the entering light fluxes L2 and L3 do not enter the pupil Ea, so that the image will be blocked.

To cope with this, according to the present embodiment, the motion of the pupil Ea is detected by image processing of the image captured by the camera 12 of the pupil detection unit 10. Then, based on the detected pupil position, the movable planar mirror 6 is rotated in the direction of the arrow A by an actuator, not illustrated. Thereby, the second focal point P2 of the ocular mirror 7 is shifted to position P6, and the first focal point P1 is correspondingly shifted to position P5. This means that the exit pupil EP is shifted from position P1 to position P5.

Furthermore, the scanning unit 5 including the scanning mirror 5a as a whole rotates, interlockingly with the rotation of the movable planar mirror 6, in the direction of the arrow B about the incident point of the light flux L1 emitted from the beam light source 3 to the scanning mirror 5a. Thereby, the entering light fluxes L2 and L3 are shifted to be L4 and L5, respectively. The entering light fluxes L2 and L4 and the entering light fluxes L3 and L5 respectively proceed toward the same position in the image to be drawn (the same image position). The light fluxes L4 and L5 are obtained by shifting in parallel the light fluxes L2 and L3 entering the pupil Ea from the ocular mirror 7. The word "parallel" used here means not only exact parallel but also a range that can be considered parallel, i.e., including a case where the slight displacement of the image position from the parallel state within a range that an observer is not aware of the displacement occurs.

The scanning unit 5 may be interlocked with the movable planar mirror 6 by transmitting the rotation of the movable planar mirror 6 to the scanning unit 5 using a mechanical interlocking mechanism such as a gear. Alternatively, an actuator dedicated to the scanning unit 5 may be electrically interlocked therewith.

As described above, the movable planar mirror 6 is rotated so as to follow the movement of the pupil Ea of the observer, whereby the entering light fluxes can be guided to the pupil Ea after the movement, thus allowing the observer to view an image free from vignetting. Moreover, the rotation of the scanning unit 5 can keep each of the entering light fluxes to the pupil Ea parallel between before and after the movement. This means that the incident angles of the entering light fluxes to the pupil Ea can be kept constant. Thus, the movement of the pupil Ea does not cause the displacement of the viewed image substantially.

When the focal point (exit pupil) of the ocular mirror 7 is shifted by the rotation of the movable planar mirror 6, if the curved surface of the ocular mirror 7 is a part of a spheroid, the optical paths of the entering light fluxes to the pupil Ea do not intersect at one point in the strict sense. In this respect, however, while the pupil Ea moves about 8 mm at the maximum, the distance between the focal points P1 and P2 of the ocular mirror 7 is as large as about 100 mm, and therefore there is no practical problem.

The reflection of the light flux by the ocular mirror 7 as the curved mirror causes optical distortion in the image. This distortion is caused also due to the rotation of the movable planar mirror 6 for following the motion of the pupil Ea and the rotation of the scanning unit 5 for keeping the incident angles of the light fluxes to the pupil Ea constant.

To cope with this, according to the present embodiment, a distortion correcting part 25 provided in a display controlling part 22 described later corrects the optical distortion electrically in accordance with the rotation position of the movable planar mirror 6 (and the scanning unit 5). Thus, the observer can always view an image free from distortion.

Meanwhile, in the present embodiment, the optical system that converges the light fluxes toward the pupil Ea so as to intersect at the exit pupil EP is constituted only by the ocular mirror 7 that has a concave surface facing the eye E of the observer. Thereby, the ocular mirror 7, that is, the image display apparatus 1 can be brought closer to the eye E. As a result, the image display apparatus 1 can be made compact and with a wide angle of view.

Figure 3:
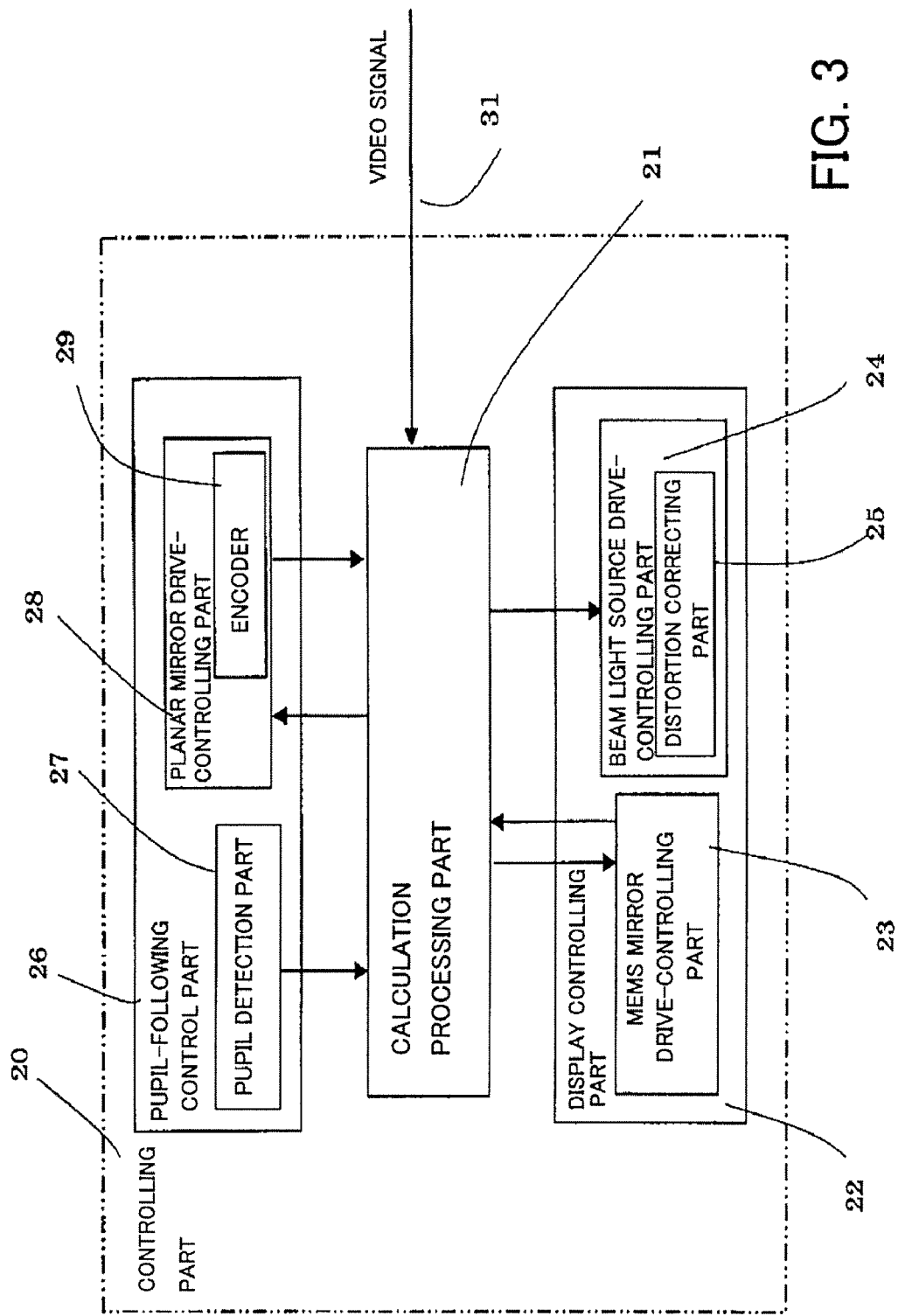
FIG. 3 is a block diagram showing the configuration of a controlling part of the retinal scanning image display apparatus of Embodiment 1.

FIG. 3 shows the configuration of the controlling part 20. The controlling part 20 is constituted by a calculation processing part 21, the display controlling part 22, and a pupil-following control part 26.

The calculation processing part 21 is constituted by a CPU (central processing unit, an IC including an interface and its peripheral circuit.

The display controlling part 22 is constituted by a MEMS mirror (scanning unit) drive-controlling part 23 and a beam light source drive-controlling part 24.

The MEMS mirror drive-controlling part 23 controls, in accordance with an instruction from the calculation processing part 21, a swing timing and a swing angle of the scanning mirror 5a in the scanning unit 5.

The beam light source drive-controlling part 24 modulates the beam light source 3 based on the video signal 31 from the image supply apparatus 100. The beam light source drive-controlling part 24 includes the distortion correcting part 25 that electrically corrects the optical distortion in the image caused due to the rotation of the movable planar mirror 6 and the scanning unit 5. The distortion correcting part 25 controls the modulating operation of the beam light source 3 so as to generate distortion in the direction opposite to the direction of the above optical distortion.

The pupil-following control part 26 is constituted by a pupil detection part 27 and a planar mirror drive-controlling part 28 that controls the rotation of the movable planar mirror 6. To control the rotation of the movable planar mirror 6 means the control of the rotation of the scanning unit 5 interlockingly therewith.

The pupil detection part 27 controls the light emission of the LEDs 11 in the pupil detection unit 10, while calculating the pupil position by image processing of the image captured by the camera 12.

The planar mirror drive-controlling part 28 controls, based on the pupil position calculated by the pupil detection part 27, the rotation of the movable planar mirror 6. The scanning unit 5 rotates interlockingly with the rotation of the movable planar mirror 6.

The planar mirror drive-controlling part 28 includes an encoder 29 that detects the rotation position of the movable planar mirror 6. The rotation position of the movable planar mirror 6 detected by the encoder 29 is sent to the calculation processing part 21. The calculation processing part 21 controls, based on the detection result of the rotation position of the movable planar mirror 6, the operation of the display controlling part 22 (the MEMS mirror drive-controlling part 23 and the beam light source drive-controlling part 24 including the distortion correcting part 25).

Embodiment 2

Figure 4:
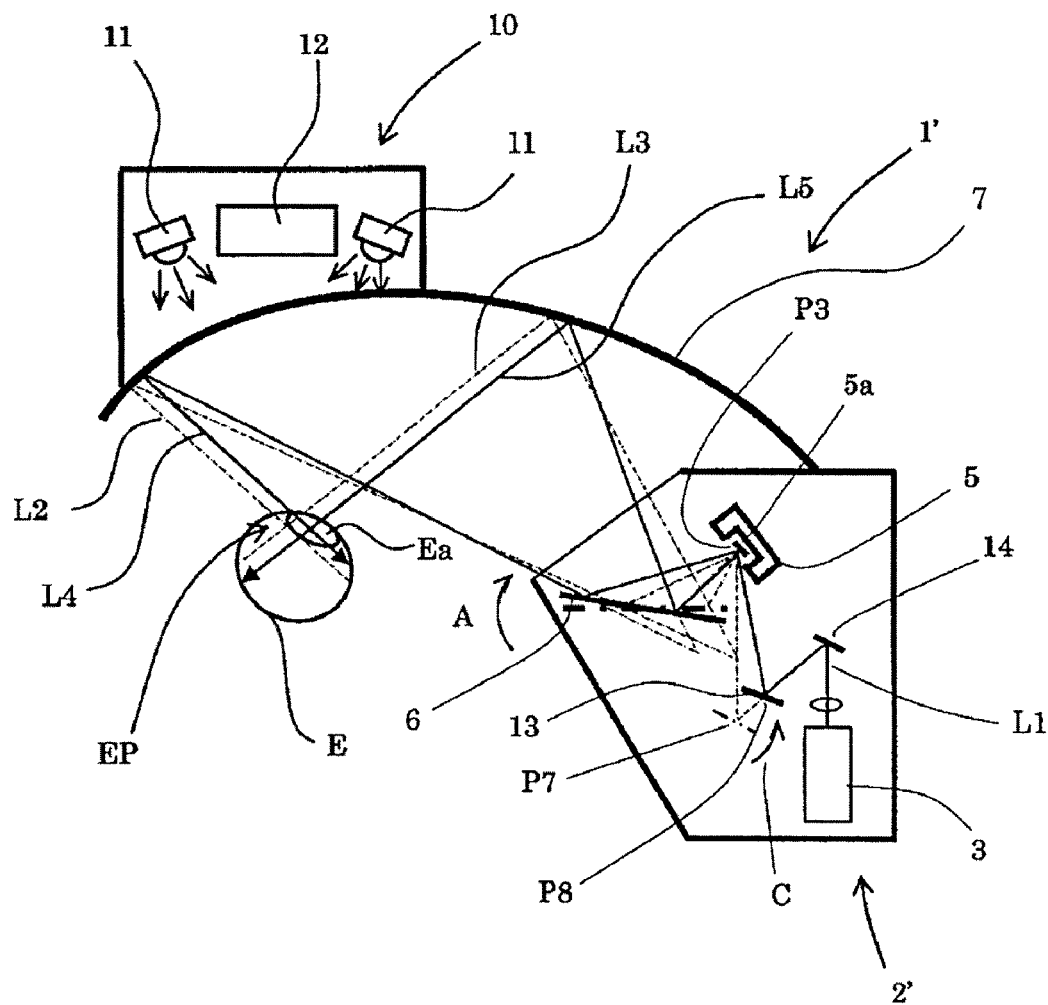
FIG. 4 shows the configuration of a retinal scanning image display apparatus that is Embodiment 2 of the present invention.

FIG. 4 shows the configuration of an image display apparatus 1' that is Embodiment 2 of the present invention.

In the above-stated Embodiment 1, the scanning unit 5 is rotated so as to keep the incident angle of the light flux to the pupil Ea constant while following the movement of the pupil Ea. On the other hand, in the present embodiment, a first movable planar mirror (a first reflective surface) 13 provided in a scanning part 2' is shifted instead of the rotation of the scanning unit 5.

In the present embodiment, the same reference numerals will be assigned to the components common to those of Embodiment 1. The movable planar mirror 6, however, is referred to as a second movable planar mirror (a second reflective surface) 6 in the present embodiment. Although not illustrated, the present embodiment also is provided with a controlling part corresponding to the controlling part 20 described in Embodiment 1.

In FIG. 4, the light flux L1 from the beam light source 3 is reflected by a fixed planar mirror 14 and the first movable planar mirror 13, and then enters the scanning unit 5. The fixed planar mirror 14 is provided for smoothly guiding the light flux L1 from the beam light source 3 disposed in the direction illustrated in the drawing to the first movable planar mirror 13. The fixed planar mirror 14 can be omitted by changing the direction of the beam light source 3.

The light flux scanned by the scanning unit 5 impinges on the ocular mirror 7 via the second movable planar mirror 6, is reflected by the ocular mirror 7 and then proceeds toward the exit pupil EP. Although the optical path of the light flux changes over time in accordance with a change of the angle of the scanning mirror 5a of the scanning unit 5, respective optical paths of the scanned light flux intersect at the exit pupil EP.

Thus, since an image is drawn on the retina of the observer whose pupil Ea is placed at the position of the exit pupil EP, the observer can view the image.

Similarly to Embodiment 1, the second movable planar mirror 6 of the present embodiment is rotated in the direction of the arrow A by the above-stated controlling part so as to follow the movement of the pupil Ea. The first movable planar mirror 13 is shifted interlockingly with the second movable planar mirror 6 while rotating from position P7 to position P8 as indicated by the arrow C. Thereby, the incident angle of the light flux can be changed without changing the incident point to the scanning mirror 5a of the scanning unit 5. In other words, the state equivalent to the state where the scanning unit 5 is rotated can be created.

Therefore, also in the present embodiment, the entering light fluxes L2 and L3 before the movement of the pupil Ea (i.e., the position of the exit pupil EP) can be shifted in accordance with the movement of the pupil Ea, so that the entering light fluxes L4 and L5 can be guided to the pupil Ea after the movement without vignetting. Furthermore, because of the effect equivalent to the rotation of the scanning unit 5, each of the entering light fluxes to the pupil Ea can be kept parallel between before and after the movement. In other words, the incident angles of the entering light fluxes to the pupil Ea can be kept constant. Thus, the movement of the pupil Ea does not cause the displacement of the viewed image substantially.

As described above, according to the present embodiment, the same effect as that obtained by the rotation of the scanning unit 5 can be obtained by the rotation and shift of the first movable planar mirror 13. As a result, the space required for driving of the first movable planar mirror 13 can be made small as compared with the case where the scanning unit 5 is directly driven, which includes various added components such as a frame portion holding the scanning mirror 5a and an electromagnetic driving circuit that swings reciprocally the scanning mirror 5a, in addition to the scanning mirror 5a. Thus, the present embodiment is advantageous for making the image display apparatus smaller.

Embodiment 3

Figure 5:
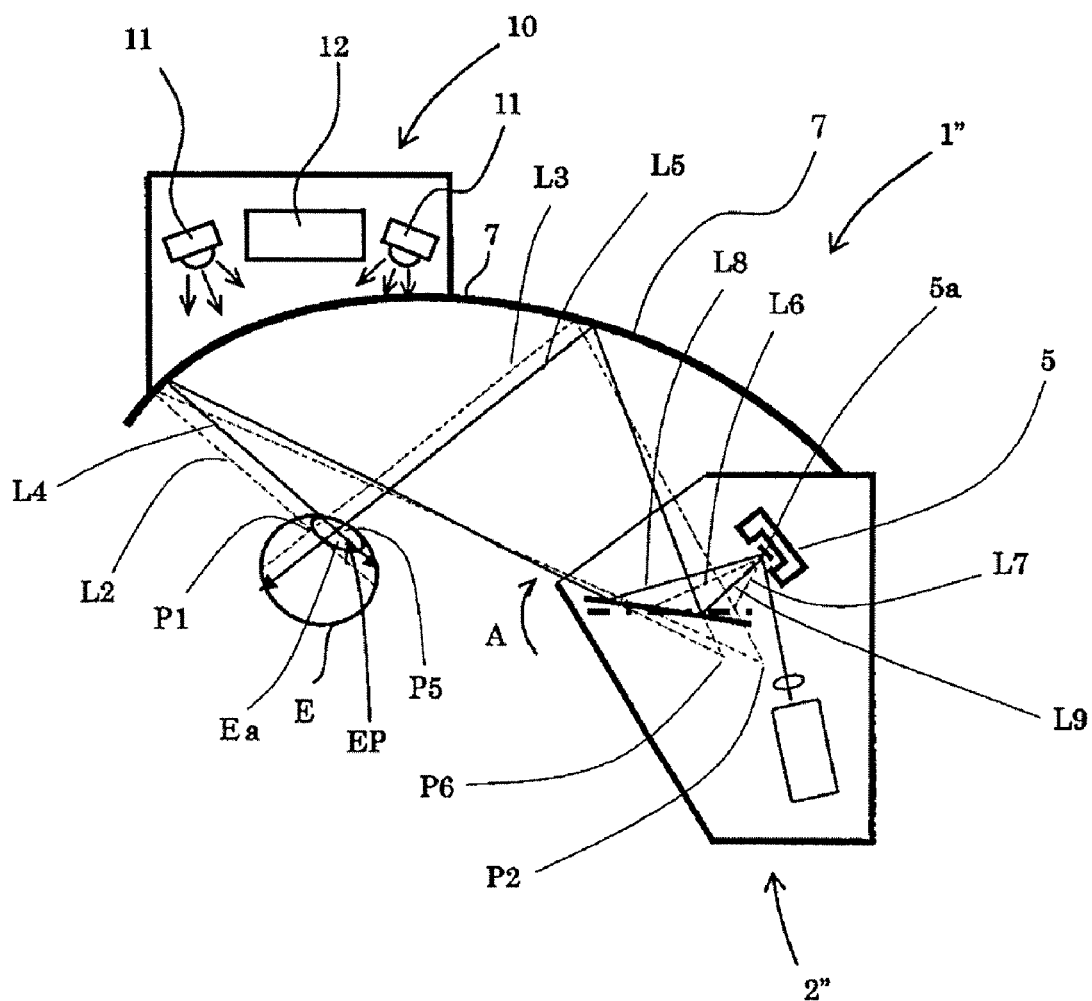
FIG. 5 shows the configuration of a retinal scanning image display apparatus that is Embodiment 3 of the present invention.
Figure 6A:
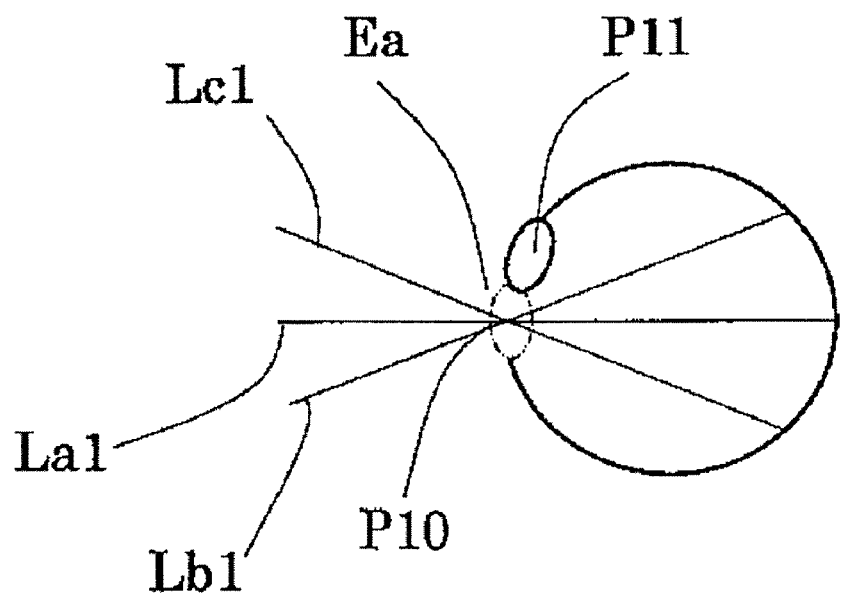
FIG. 6A is for explaining a conventional retinal scanning image display apparatus.
Figure 6B:
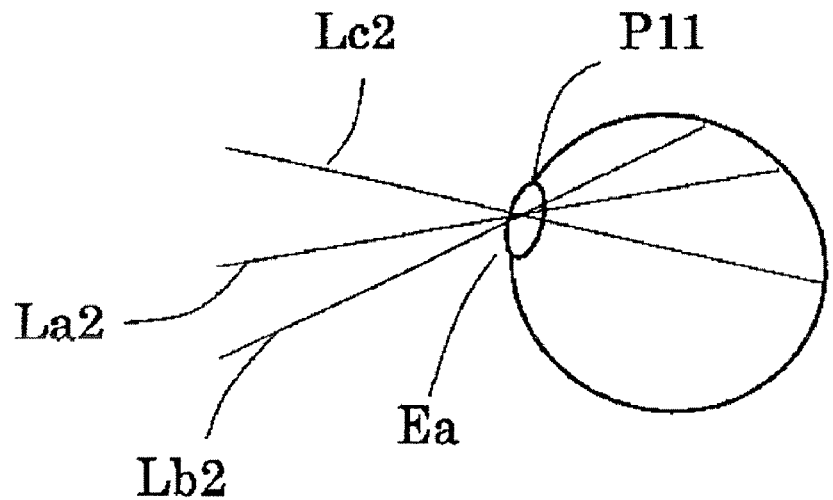
FIG. 6B is for explaining the conventional retinal scanning image display apparatus.
Figure 6C:
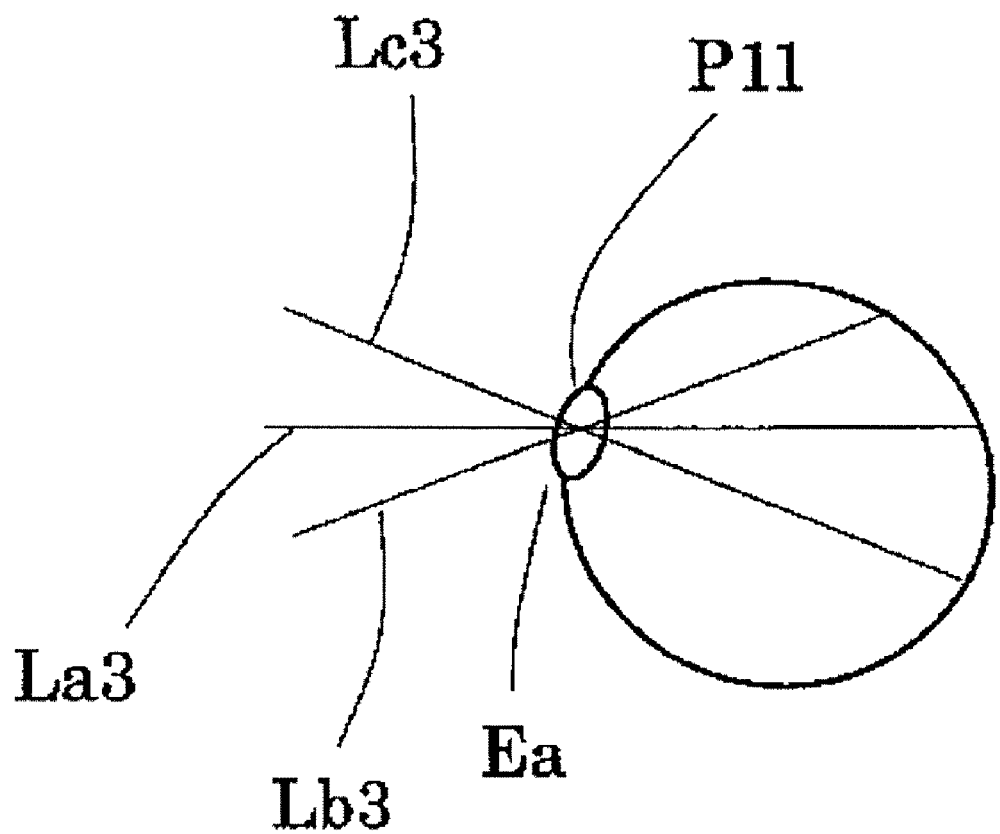
FIG. 6C is for explaining the conventional retinal scanning image display apparatus.
Figure 7:
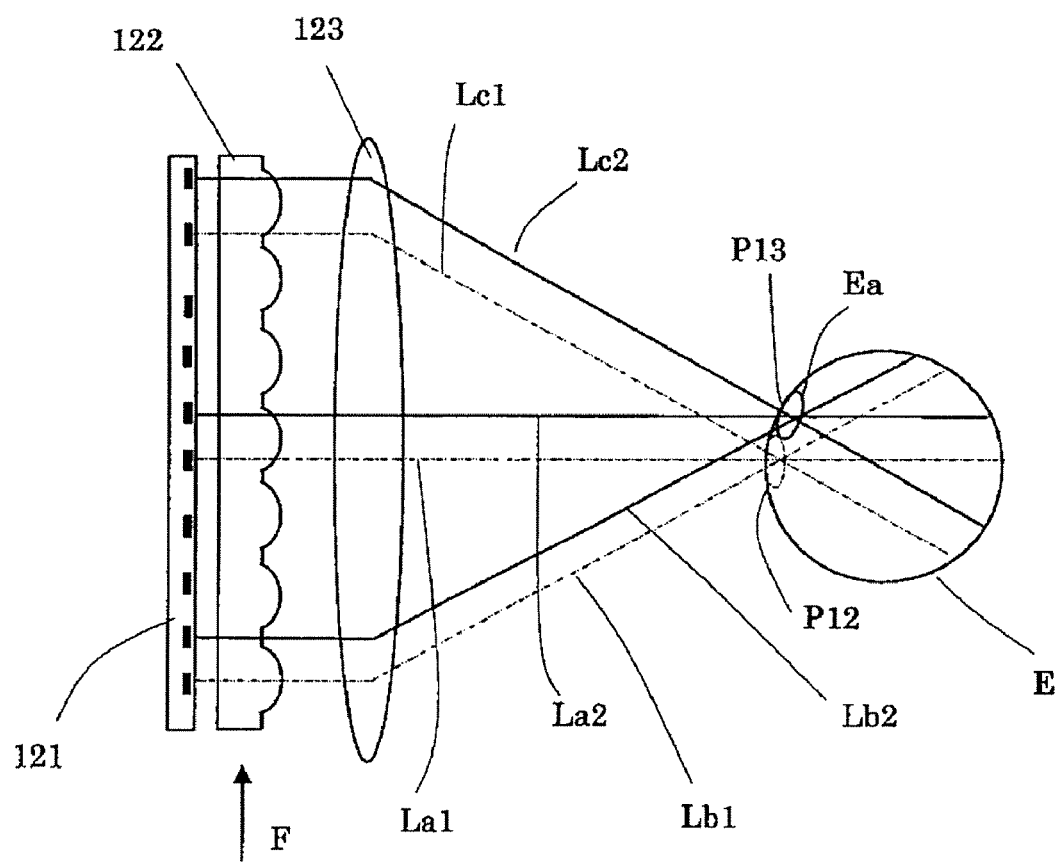
FIG. 7 shows the configuration of another conventional retinal scanning image display apparatus.

FIG. 5 shows the configuration of an image display apparatus 1" that is Embodiment 3 of the present invention. In the above-stated Embodiment 1, the scanning unit 5 is rotated so as to keep the incident angles of the light fluxes to the pupil Ea constant while following the movement of the pupil Ea. On the other hand, in the present embodiment, the drawing timing of the image is controlled instead of rotating the scanning unit 5. More specifically, the light-emitting timing of a beam light source 3 in a scanning part 2' is controlled.

In the present embodiment, the same reference numerals will be assigned to the components common to those of Embodiment 1. The optical paths of the scanned light flux guided from the beam light source 3 to the eye E of the observer are the same as those in Embodiment 1. Although not illustrated, the present embodiment also is provided with a controlling part corresponding to the controlling part 20 described in Embodiment 1.

In the present embodiment, when the pupil Ea shifts from position P1 to position P5, then the above-described controlling part causes the movable planar mirror 6 to rotate in the direction of the arrow A. Thereby, the converging position of the light fluxes (intersecting position of the optical paths of the scanned light flux) can follow the movement of the pupil Ea.

At this time, the light fluxes L2 and L3 are shifted in parallel to be light fluxes L4 and L5 without changing the incident angles of the entering light fluxes L2 and L3 to the pupil Ea. To this end, in the present embodiment, the light-emitting timing of the beam light source 3 for the swing (operation) of the scanning mirror 5a is controlled so that the light flux L6 emitted from the scanning unit 5 becomes the light flux L8 and the light flux L7 becomes the light flux L9.

In the present embodiment also, the entering light fluxes L2 and L3 before the movement of the pupil Ea (i.e., the position of the exit pupil EP) can be shifted in accordance with the movement of the pupil Ea, so that the entering light fluxes L4 and L5 can be guided to the pupil Ea after the movement without vignetting. Furthermore, because of the effect equivalent to the rotation of the scanning unit 5 that is obtained from the control of the light-emitting timing of the beam light source 3, each of the entering light fluxes to the pupil Ea can be kept parallel between before and after the movement. In other words, the incident angles of the entering light fluxes to the pupil Ea can be kept constant. Thus, the movement of the pupil Ea does not cause the displacement of the viewed image substantially.

In the present invention, there is a need to increase the swing angle of the scanning mirror 5a as compared with Embodiments 1 and 2. However, this does not mean the upsizing of the apparatus as compared with the case where the display panel is increased in size for changing an image display position on the display panel as required in conventional apparatuses, and therefore the present embodiment is advantageous in terms of the cost as well.

As described above, according to the above embodiments, the light flux scanned by the scanning unit can be guided to the eye of the observer so as to follow the movement of the eye (the pupil) of the observer, while always keeping the incident angle of each of the entering light fluxes to the eye constant. Therefore, a retinal scanning image display apparatus substantially free from the vignetting of the image or a change of the image position can be realized even when the eye of the observer moves.

Furthermore, the present invention is not limited to these embodiments and various variations and modifications may be made without departing from the scope of the present invention.

This application claims foreign priority benefits based on Japanese Patent Application No. 2006-332261, filed on Dec. 8, 2006, which is hereby incorporated by reference herein in its entirety as if fully set forth herein.

What is claimed is:

1. A retinal scanning image display apparatus comprising:
a light source that emits a light flux modulated in accordance with a video signal;
a scanning unit that scans a light flux from the light source;
a reflective surface that reflects the light flux from the scanning unit;
an ocular unit that guides the light flux from the reflective surface to an eye of an observer to project an image generated from the video signal on a retina thereof; and
a control unit that controls the scanning unit to scan the light flux two-dimensionally;
wherein optical paths of the light flux scanned by the scanning unit intersect at an exit pupil position of the ocular unit, which is where a pupil of the eye is positioned,
wherein each of the scanning unit as a whole and the reflective surface is shiftable, and
wherein the control unit controls shifting of both the scanning unit as a whole and the reflective surface in accordance with motion of the eye so that the optical paths of the scanned light flux toward the exit pupil position are respectively moved in parallel to move the intersecting position of the optical paths at the exit pupil position to maintain a position of the projected image on the retina.

2. An image display apparatus according to claim 1, wherein the scanning unit as a whole and the reflective surface are pivotable interlockingly with each other.

3. An image display apparatus according to claim 1, wherein the reflective surface is a planar reflective surface.

4. An image display apparatus according to claim 1, further comprising:
a detector that detects the motion of the eye,
wherein the control unit controls shifting of both the scanning unit as a whole and the reflective surface in accordance with the motion of the eye detected by the detector.

5. A retinal scanning image display apparatus comprising:
a light source that emits a light flux modulated in accordance with a video signal;
a first reflective surface configured to reflect a light flux from the light source;
a scanning unit that scans the light flux from the first reflective surface;
a second reflective surface configured to reflect the light flux from the scanning unit;
an ocular unit that guides the light flux from the second reflective surface to an eye of an observer to project an image generated from the video signal on a retina thereof; and
a control unit that controls the scanning unit to scan the light flux two-dimensionally,
wherein optical paths of the light flux scanned by the scanning unit intersect at an exit pupil position of the ocular unit, which is where a pupil of the eye is positioned,
wherein each of the first and second reflective surfaces is shiftable, and
wherein the control unit controls shifting of both the first and second reflective surfaces in accordance with motion of the eye so that the optical paths of the scanned light flux toward the exit pupil position are respectively moved in parallel to move the intersecting position of the optical paths at the exit pupil position to maintain a position of the projected image on the retina.

6. An image display apparatus according to claim 5, wherein the first and second reflective surfaces are pivotable interlockingly with each other.

7. An image display apparatus according to claim 5, wherein the first and second reflective surfaces are planar reflective surfaces.

8. An image display apparatus according to claim 5, further comprising:
a detector that detects the motion of the eye,
wherein the control unit controls shifting of the first and second reflective surfaces in accordance with the motion of the eye detected by the detector.

9. A retinal scanning image display apparatus comprising:
a light source that emits a light flux modulated in accordance with a video signal;
a scanning unit that scans a light flux from the light source;
a reflective surface that reflects the light flux from the scanning unit;
an ocular unit that guides the light flux from the reflective surface to an eye of an observer to project an image generated from the video signal on a retina thereof; and
a control unit that controls the scanning unit to scan the light flux two-dimensionally,
wherein optical paths of the light flux scanned by the scanning unit intersect at an exit pupil position of the ocular unit, which is where a pupil of the eye is positioned,
wherein the reflective surface is shiftable, and
wherein the control unit changes a light-emitting timing of the light source for operation of the scanning unit and controls shifting of the reflective surface in accordance with motion of the eye so that the optical paths of the scanned light flux toward the exit pupil position are respectively moved in parallel to move the intersecting position of the optical paths at the exit pupil position to maintain a position of the projected image on the retina.

10. An image display apparatus according to claim 9, wherein the reflective surface is rotatable.

11. An image display apparatus according to claim 9, wherein the reflective surface is a planar reflective surface.

12. An image display apparatus according to claim 9, further comprising:
a detector that detects the motion of the eye,
wherein the control unit changes a light-emitting timing of the light source with reference to an operation of the scanning unit, while controlling shifting of the reflective surface in accordance with the motion of the eye detected by the detector.

* * * * *